US006467477B1

(12) United States Patent
Frank et al.

(10) Patent No.: US 6,467,477 B1
(45) Date of Patent: Oct. 22, 2002

(54) BREATH-BASED CONTROL OF A THERAPEUTIC TREATMENT

(75) Inventors: John Frank, Harrison City; Peter D. Hill, Monroeville, both of PA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 09/525,786

(22) Filed: Mar. 15, 2000

Related U.S. Application Data
(60) Provisional application No. 60/126,306, filed on Mar. 26, 1999.

(51) Int. Cl.[7] ................................................ A61M 16/00
(52) U.S. Cl. .......................... 128/203.23; 128/204.18
(58) Field of Search ...................... 128/200.24, 204.18, 128/204.21, 204.23, 204.26, 204.12, 207.14

(56) References Cited

U.S. PATENT DOCUMENTS

| | | | |
|---|---|---|---|
| 5,044,362 A | 9/1991 | Younes | |
| 5,107,830 A | 4/1992 | Younes | |
| 5,117,819 A | 6/1992 | Servidio et al. | |
| 5,148,802 A | 9/1992 | Sanders et al. | |
| 5,199,424 A | 4/1993 | Sullivan et al. | |
| 5,203,343 A | 4/1993 | Axe et al. | |
| 5,239,995 A | 8/1993 | Estes et al. | |
| 5,245,995 A | 9/1993 | Sullivan et al. | |
| 5,353,788 A | 10/1994 | Miles | |
| 5,413,111 A | * 5/1995 | Wilkinson | 128/724 |
| 5,433,193 A | 7/1995 | Sanders et al. | |
| 5,492,113 A | 2/1996 | Estes et al. | |
| 5,522,382 A | * 6/1996 | Sullivan et al. | 128/204.23 |
| RE35,295 E | * 7/1996 | Estes et al. | 128/204.23 |
| 5,535,738 A | 7/1996 | Estes et al. | |
| 5,540,219 A | * 7/1996 | Mechlenburg et al. | 18/204.23 |
| 5,551,418 A | 9/1996 | Estes et al. | |
| 5,682,878 A | 11/1997 | Ogden | |
| 5,823,187 A | 10/1998 | Estes et al. | |
| 6,029,665 A | * 2/2000 | Bethon-Jones | 128/204.23 |
| 6,105,575 A | * 8/2000 | Estes et al. | 128/204.23 |
| 6,131,571 A | * 10/2000 | Lampotang et al. | 128/204.21 |
| 6,152,129 A | * 11/2000 | Berthon-Jones | 128/200.24 |
| 6,269,811 B1 | * 8/2001 | Duff et al. | 128/204.21 |

* cited by examiner

*Primary Examiner*—Aaron J. Lewis
*Assistant Examiner*—Teena Mitchell
(74) *Attorney, Agent, or Firm*—Michael W. Haas (57) ABSTRACT

A system and method for providing a therapeutic treatment, such as a flow of breathing gas, to a patient at variable treatment levels. A respiratory cycle monitor detects the patient's respiratory cycles and a control unit incrementally adjusts the treatment level from a first predetermined level to a second predetermined level over a first predetermined number of respiratory cycles. The amount of the incremental adjustment and the frequency of such adjustments over the course of the first predetermined number of respiratory cycles can be controlled to achieve a desired change in the therapeutic treatment over the course of the patient's respiration.

33 Claims, 7 Drawing Sheets

BREATH-BASED CONTROL OF A THERAPEUTIC TREATMENT

CROSS-REFERENCE TO RELATED APPLICATIONS

The present invention claims priority under 35 U.S.C. §119(e) from U.S. provisional patent application No. 60/21126,306 filed Mar. 26, 1999.

BACKGROUND OF THE INVENTION

1. Field of the Invention

The present invention pertains to a system and method for providing a therapeutic treatment to a patient, and, in particular, to a system and method in which the level of therapeutic treatment incrementally transitions between two predetermined levels by a predetermined amount over successive patient breathing cycles.

2. Description of the Related Art

It is well known to administer a therapeutic treatment to a patient in which the level of treatment being provided to the patient changes from a first level to a second level over a predetermined period of time. For example, devices exist that deliver a supply of breathing gas to the airway of patient in which the pressure level of the supply of breathing gas increases or ramps from a relatively low base pressure to a higher prescribed pressure level over a fixed or variable period of time, typically referred to as a ramp period. See, e.g., U.S. Pat. Nos. 5,239,995; Re. 35,295; U.S. Pat. Nos. 5,492,113; 5,551,418 and 5,823,187 all to Estes et al. and U.S. Pat. No. 5,117,819 to Servidio et al. Other U.S. Patents that teach automatically increasing the pressure level of air delivered to the patient over a variable period of time until the pressure reaches a preset operating level include U.S. Pat. No. 5,522,382 to Sullivan et al.

As noted above, each of these patents specifically define the ramp period, i.e., the period of time it takes to transition from the low to high pressure, as being based on a fixed or variable period of time, which is set and measured using a timer. For example, the ramp function for a conventional continuous positive airway pressure (CPAP) device is typically set to a low level of 3–5 $cmH_2O$ and gradually increases to the final prescribed value over a set period of time, which is usually between 5–45 minutes following the initiation of the CPAP therapy. Delivering a pressure at an initial low level and gradually increasing the pressure over the course of the ramp period at the beginning of the CPAP therapy allows the patient time to fall asleep at the lower, more comfortable, pressure, and, once asleep, provides the patient with the higher prescribed pressure necessary to treat the patient's respiratory disorder, such as obstructive sleep apnea (OSA).

There are disadvantages with the above-described time-based conventional techniques for varying the treatment level, such as a pressure support therapy, provided to a patient. For example, the time-based pressure ramp is not well suited to ventilatory applications, where the patient does not need time to fall asleep, but wants some delay in reaching the final prescribed pressure level to adjust the mask and/or synchronize the ventilator to their breathing pattern. The above-described time-based system also does not automatically take into consideration the respiratory requirements of each particular patient. For example, a thirty second ramp may be a sufficient amount of time for many patients on a ventilator to make the necessary adjustments. If, however, the patient is breathing rapidly, the fixed thirty second delay may be too long a delay before providing the needed pressure support, thereby causing the patient some distress while they breathe rapidly and wait for the ventilator to reach the prescribed pressure level. Shorter time periods, on the other hand, may not provide the patient with enough time to perform the desired mask adjustments and ventilator synchronization.

It can also be appreciated that a time-based technique for setting the duration over which a therapeutic treatment varies between a low level to a high level is insensitive to the different needs of the overall patient population. For example, patients that breathe relatively fast may want increased pressure support sooner than patients that breathe at a relatively slow breathing rate. In which case, timer based techniques require the caregiver to recognize the particular nuisances of each patient and adjust the ventilator or pressure support device accordingly. This places a relatively large burden on the respiratory technician and may not maximize the comfort of the patient receiving respiratory assistance.

SUMMARY OF THE INVENTION

Accordingly, it is an object of the present invention to provide a patient treatment system that overcomes the shortcomings of conventional treatment systems. This object is achieved according to one embodiment of the present invention by providing a patient treatment system that, in its most general sense, includes a treatment system for providing a therapeutic treatment to a patient at variable treatment levels and a respiratory cycle monitoring system to detect a respiratory cycle of the patient so that the treatment system can discern the patient's separate respiratory cycles. In addition, the treatment system includes a treatment modifying system that changes the treatment level being provided to the patient from a first predetermined treatment level to a second predetermined treatment level over a first predetermined number of respiratory cycles of the patient by adjusting an output of the treatment system a first predetermined amount over a second predetermined number of respiratory cycles of the patient.

In a preferred embodiment of the present invention, the treatment system is a system for delivering a flow of breathing gas to a patient, the respiratory cycle monitoring system is a sensor that monitors a physiological characteristic of the patient indicative of a respiratory cycle, and the treatment modifying system causes the output of the breathing gas delivering system to transition from either a first predetermined pressure or a first predetermined flow to either a second predetermined pressure or a second predetermined flow over the first predetermined number of respiratory cycles by adjusting an output of the system for delivering breathing gas by the first predetermined amount over the second predetermined number of patient respiratory cycles.

It is yet another object of the present invention to provide a method of providing a therapeutic treatment to a patient that does not suffer from the disadvantages associated with conventional treatment methods. This object is achieved by providing a method that includes providing a therapeutic treatment to a patient at variable treatment levels, detecting a respiratory cycle of the patient, and changing the treatment level from a first predetermined treatment level to a second predetermined treatment level over a first predetermined number of patient respiratory cycles by adjusting a treatment level by a first predetermined amount over a second predetermined number of respiratory cycles.

In another preferred embodiment for the method of treating a patient, the step of providing a therapeutic treatment includes delivering a flow breathing gas to a patient and the detecting step includes monitoring, via a sensor, a physiological characteristic of the patient indicative of a respiratory cycle. In addition, the step of changing the treatment level includes transitioning either a pressure or a flow of breathing gas from either a first predetermined pressure or a first predetermined flow to one of a second predetermined pressure or a second predetermined flow over the first predetermined number of respiratory cycles by adjusting either the flow or pressure of said breathing gas by the first predetermined amount over the second predetermined number of respiratory cycles.

Still another object of the present invention is to provide a system or method of treating a patient in which the gain, base pressure or base flow used to compute the pressure of breathing gas to be delivered to the patient is altered over a predetermined number of breathing cycles of the patient, thereby varying the flow or pressure support provided to the patient between two set levels.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
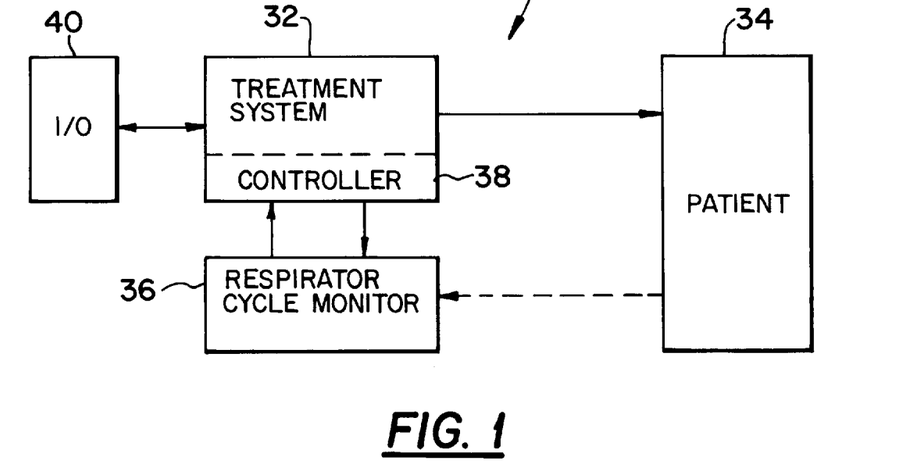
FIG. 1 is a schematic diagram of a patient treatment system according to the principles of the present invention.

FIG. 1 schematically illustrates an exemplary embodiment of a patient treatment system 30 according to the principles of the present invention. Patient treatment system 30, in its most general sense, includes a treatment system 32 for providing a therapeutic treatment to a patient 34. In addition, a respiratory cycle monitoring system 36 associated with treatment system 32 monitors the patient or treatment system 32 to detect the respiratory cycles of patient 34. The respiratory cycle monitoring system includes a device for detecting the respiratory cycles of the patient and for providing a signal indicative of the respiratory cycle to a controller 38 in treatment system 32. In an exemplary embodiment of the present invention, controller 38 is a processor that maintains a count of the number of respiratory cycles based on the information provided by respiratory cycle monitoring system 36.

Controller 38 also functions as a treatment modifying system to incrementally change or ramp the treatment level provided by treatment system 32 from a first predetermined treatment level to a second predetermined treatment level over a first predetermined number of respiratory cycles of the patient. In an exemplary embodiment of the present invention, an input/output device 40 associated with treatment system 32 is used to control, either directly or indirectly, the amount of each incremental adjustment in controller 38, as well as the first and second treatment levels. In addition, the input/output device can provide an indication, such as visual light, indicating that the ramp function has been selected and/or that the ventilator or pressure support device is currently operating in the ramp mode.

Controller 38 causes the treatment level to change after the elapse of a second predetermined number of respiratory cycles, such as after each respiratory cycle, which is a fraction of the first predetermined number of respiratory cycles. This second predetermined number of respiratory cycles can be set automatically by controller 38 or manually via input/output device 40. The controller alters the treatment level by the predetermined amount after the second predetermined number of breathing cycles has taken place until the treatment level as changed from the first predetermined treatment level to the second predetermined treatment level.

The present invention contemplates that treatment system 32 is any device or combination of devices that provide a therapeutic treatment to a patient. For example, in the embodiments discussed in greater detail below, treatment system 32 is a ventilation/pressure support system that delivers a flow a breathing gas to the airway of the patient at variable pressures or flow rates. It is to be understood, however, that treatment system 32 be other devices that provide a therapeutic treatment to a patient, such as a device to administer a flow of medication to the user, which is typically done intravenously or through the respiratory system in the form of a nebulizer. Treatment system 32 can also be a system for providing an electrical or magnetic stimulation to the patient, which are techniques used to treat respiratory disorders.

Respiratory cycle monitoring system 36 is any device or combination of devices that detect a patient's respiratory cycle. This requires detecting enough information associated with the respiratory cycle to be able to discern when the patient has complete a respiratory cycle. For example, the present invention contemplates detecting information such as a maximum, minimum, and/or zero crossing for the flow, pressure, or volume of the patient's respiration. This information can then be used to determine whether the patient has completed a respiratory cycle. It is not critical that the respiratory cycle monitoring system be able to discern the entire respiratory cycle or even which portion of the respiratory cycle the patient is in, merely that a respiratory cycle, or a portion of a respiratory cycle, has elapsed. This information is used to determine when the patient has completed a respiratory cycle so that the controller can keep count the number respiratory cycles of the patient. For example, the system can detect a relatively rapid flow to the patient. From this, it can be deduced that an inspiration has taken place and that each inspiration represents the completion of a prior respiratory cycle. Of course, other considerations, such as patient coughing can be taken into account in determining if a respiratory cycle has actually elapsed.

For example, it is known to detect sounds associated with a patient's respiration. These sounds can be used to determined when the patient has completed a respiratory cycle or a portion of a respiratory cycle. Thus, one embodiment of the present invention contemplates using an acoustic system, such as one or more microphones positioned on or near the patient or associated with the treatment system, as taught, for example in U.S. Pat. No. 5,540,219 to Mechlenburg et al., the contents of which are incorporated hereby by reference, to detect the patient's respiratory sounds. Although U.S. Pat. No. 5,540,219 teaches detecting sounds associated with airway obstruction, this technology can be adapted to detect sounds associated with respiration for purposes of detecting the patient's respiration.

The present invention also contemplates using a motion detecting system, which detects the movement of a patient associated with a patient's respiration, such as the rise and fall of the chest, as respiratory cycle monitoring system 36. Other suitable systems to detect patient respiration include a temperature detecting system that detects temperature variations associated with a patient's respiration. For example, it is known to provide a thermister at or near the patient's airway to detect the heat associated with the expired air from the patient. Thus, when heat is detect by such a sensor, this indicates that the patient as reached the expiratory phase of the respiratory cycle. See, for example, U.S. Pat. Nos. 5,190,048 and 5,413,111 both to Wilkinson, the contents of which are incorporated herein by reference. In addition, respiratory cycle monitoring system 36 can be an electrical signal sensing system that detects the electrical activity of a patient associated with a patient's respiration, such as the EMG signal from the diaphragm.

As noted above, in an exemplary embodiment of the present invention, treatment system 32 is a ventilation/pressure support system that delivers a flow a breathing gas to the airway of the patient. In such a system, the respiratory cycle monitoring system 36 is preferably a pressure sensing system associated with the patient's respiratory system that detects pressure variations induced by patient respiration, or a flow sensing system associated with the patient's respiratory system that detects flows induced by patient respiration. It is also known that the operation of a pressure support treatment system, such the power consumed by a motor driving a blower used to provide a flow of breathing gas to the patient, can change as a result of patient respiration. These changes can be detected and used to identify the occurrence of the patient respiration.

Input/output device 40 is any device suitable to provide information and/or commands to controller 38 via a hardwire or wireless connection and to present information to a user in a human perceivable format. Examples of a suitable input/output device includes a keypad, keyboard, touch pad, mouse, visual display (e.g, LCD or LED screen), microphone, speaker, switches, button, dials, lamps, or any other devices that allow a user to input information to and receive information from the treatment system.

Figure 2:
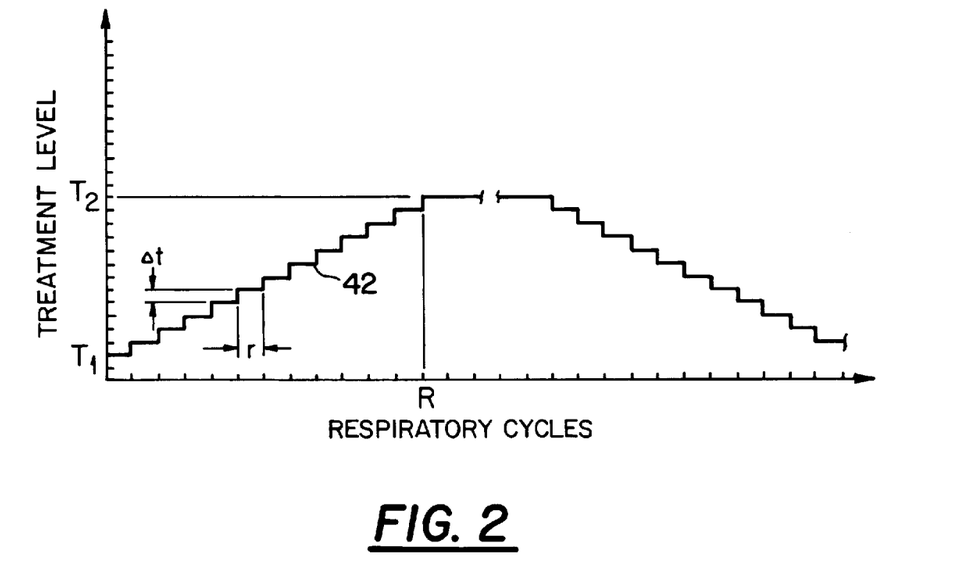
FIGS. 2 and 3 are waveforms illustrating examples of changes in a therapeutic treatment level over a plurality of patient breaths provided by the patient treatment system of FIG. 1.
Figure 3:
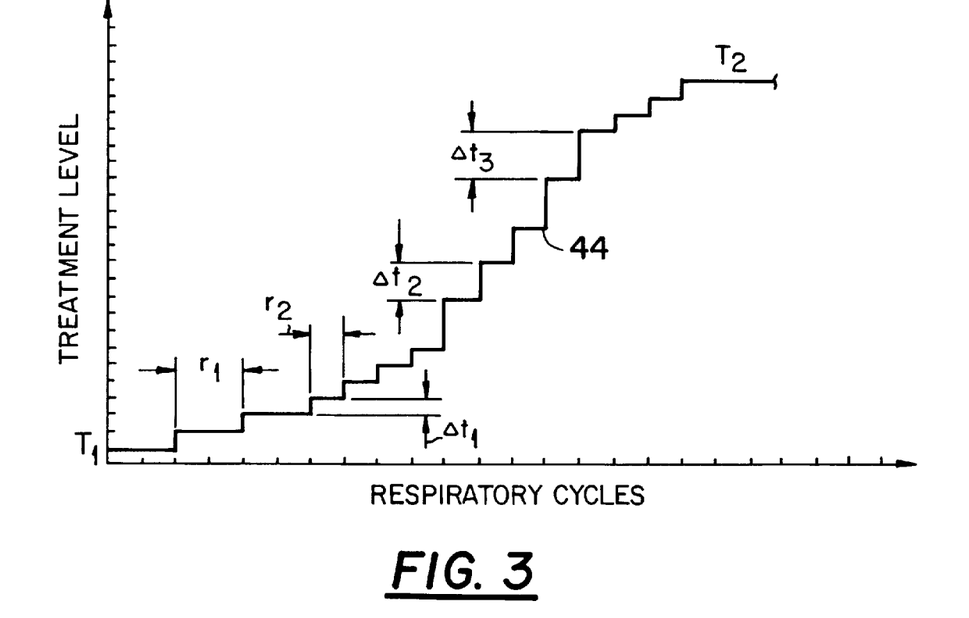

Details of the patient treatment system 30 and its operation are discussed below with reference to FIGS. 2 and 3, which are charts illustrating how the patient treatment system controls the treatment level provided to the patient over the patient's respiratory cycles. In its most basic form, the controller causes the output of the patient treatment system to vary by a fixed incremental amount $\Delta t$ over a number r of respiratory cycles. In FIG. 2, r is equal to 1. The result of such a variation in the treatment level is a relatively linear ramp function 42 for the treatment level-respiratory cycle count relationship, in which the treatment level varies between a first predetermined treatment level $T_1$ and a second predetermined treatment level $T_2$, which are set in advance. As shown in FIG. 3, the change in treatment level can include a decrease from a maximum level to a minimum level, which are also preset in advance.

In addition to setting first predetermined treatment level $T_1$ and a second predetermined treatment level $T_2$, the present invention contemplates that the incremental amount $\Delta t$ of change in the treatment level, the number of respiratory cycles r associated with each incremental change, and the total number of respiratory cycles R in the ramp can be set manually via the input/output device. Alternatively, the present invention contemplates that if first predetermined treatment level $T_1$, second predetermined treatment level $T_2$, number of respiratory cycles r associated with each incremental change, and total number of respiratory cycles R in the ramp are set in advance, the incremental amount $\Delta t$ can be calculated by the controller.

It can be appreciated that a wide variety of ramp functions are possible depending on the parameters selected for the variables $T_1$, $T_2$, $\Delta t$, r, and R used to control the flow or pressure to the patient. FIG. 3 illustrates a ramp function 44 illustrating how the shape of the ramp can be controlled by selecting different values for $\Delta t$ and r. In FIG. 3, $r_1=2$ respiratory cycles, $r_2$=one respiratory cycle, $\Delta t_1=1$ incremental amount, $\Delta t_2=2$ incremental amounts, and $\Delta t_3=3$ incremental amounts. By controlling these variables, the treatment system of the present invention can achieve a large number of treatment level versus respiratory cycle count ramp functions, including, for example, linear, exponential, raised cosine and square root functions, to control, with a relatively high degree of flexibility, the how the treatment level provided to the patient changes over the R number of patient respiratory cycles. The present invention also contemplates that input/output system 40 be used to present the user with a number of ramp function selections, so that the user can select the desired ramp function. For example, U.S. Pat. No. 5,682,878 to Ogden, the contents of which are incorporated hereby by reference, teaching selecting a time-based ramp function. This same principle can be applied to the respiratory-cycle based ramp function control of the present invention.

An exemplary embodiment of the present invention will now be discussed below with reference to FIGS. 4–7D. The patient treatment system in this embodiment is a system 46 for delivering a flow of breathing gas to a patient in which the flow of breathing gas is delivered to the patient at pressures that are greater than ambient atmosphere to ventilate the patient or to treat a breathing disorder, such as sleep apnea. In the illustrated embodiment, breathing gas delivery system 46 includes a pressure/flow generating system 48 that provides a supply of breathing gas 50 to patient 34 at a selectable pressure or a selectable flow. Breathing gas delivery system 46 also includes a patient interface assembly 52 operatively coupled to pressure/flow generating system 48 to communicate the supply of breathing gas 50 from pressure/flow generating system 48 to an airway of patient 34. It is to be understood that patient interface assembly 52 includes all components necessary to transport the flow of breathing gas from the unit where the flow is created to the airway of a patient.

Figure 4:
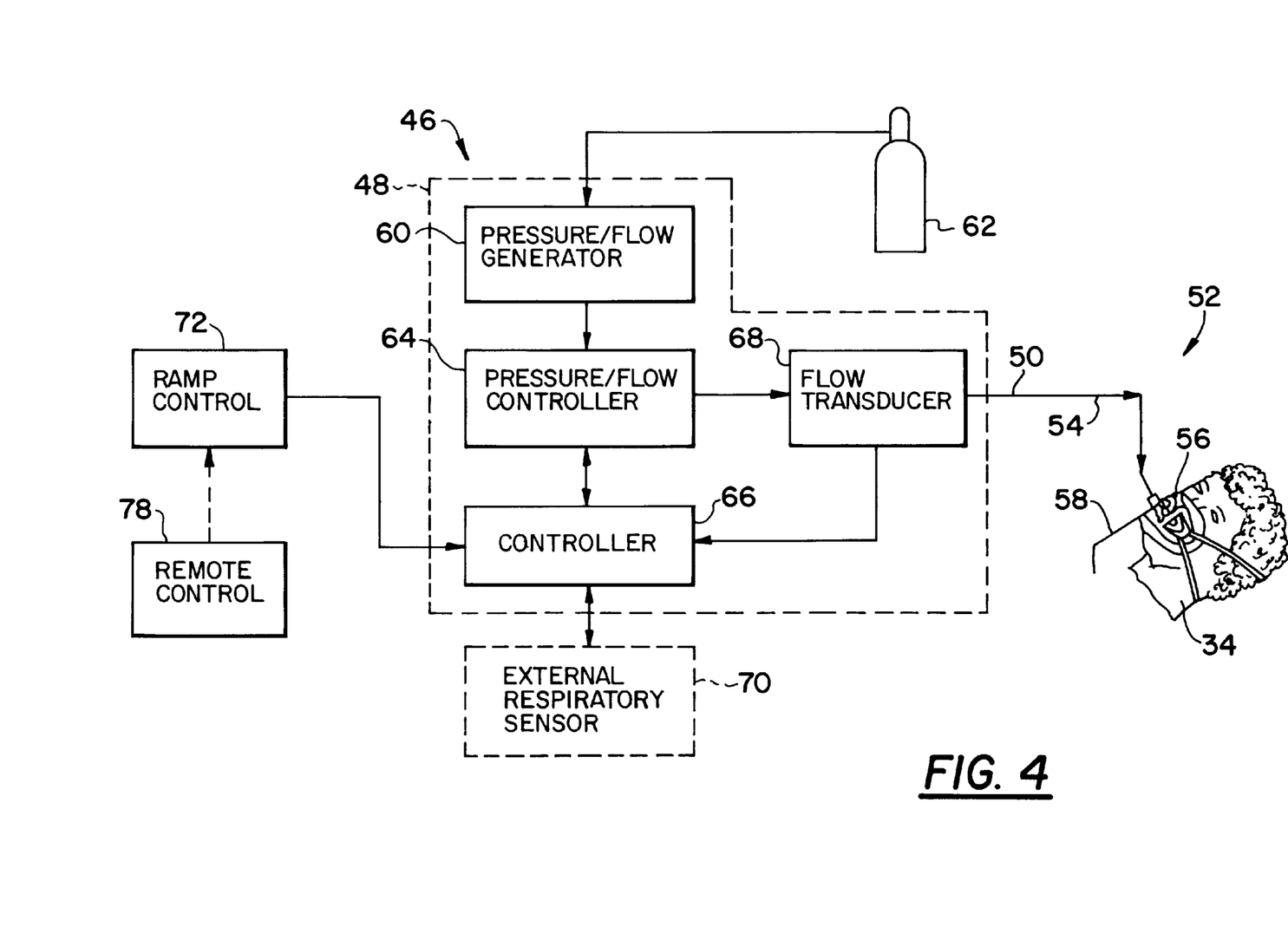
FIG. 4 is a schematic diagram of a pressure support system as the patient treatment system according to the principles of the present invention.

In one embodiment, patient interface assembly 52 includes a single flexible conduit 54 that carries the flow of breathing gas 50 to a patient interface device 56. Patient interface device 56 is any appliance, either invasive or non-invasive, such as a nasal mask, nasal/oral mask, total face mask, nasal cannula, endotracheal tube, or tracheal tube, suitable for communicating a supply of breathing gas to the airway of a patient. The patient interface device and/or conduit 54 includes a suitable exhaust port 58 for exhausting breathing gas from patient interface assembly 52 during expiration. Exhaust port 58 is preferably a passive exhaust port in the form of a continuously open port that imposes a flow restriction on the exhaust gas to permit control of the pressure of gas within the patient interface assembly 52 including providing positive end expiratory pressure (PEEP) to the patient. It is to be understood, however, that exhaust port 58 can be an active exhaust port that assumes different configurations to control the exhaust rate.

The present invention also contemplates that the patient interface assembly can be a two-limb circuit, which is common in conventional volume or pressure ventilators. The first limb, like conduit 54, delivers breathing gas to the patient, except that it lacks an exhaust port. Instead, the second limb carries the exhaust gases from the patient to ambient atmosphere. Typically, an active exhaust port in the second limb under the control of pressure/flow generating system 48 provides the desired level of PEEP to the patient. In addition, patient interface assembly 52 can include other conventional devices, such as a humidifier, heater, bacteria filter, temperature sensor, pressure sensor, flow sensor, humidity sensor, and a gas sensor, e.g., a capnometer, that measure, monitor, adjust and/or control the flow of gas to the patient.

In an exemplary embodiment of the present invention, pressure/flow generating system 48 includes a pressure/flow generator 60 that receives a supply of breathing gas, which can be oxygen or an oxygen mixture, including air, from any suitable source 62, such as a pressurized tank of gas or ambient atmosphere. Pressure/flow generator 60 is a device that elevates the pressure of the gas or that generates a flow of such gas so that the elevated pressure gas or gas flow can be delivered to the patient. An example of a suitable pressure/flow generator is a piston, bellows or blower. It is to be understood, however, that pressure/flow generator 60 can be eliminated if the gas pressure or flow from the gas source is at a sufficient pressure or flow rate so that it does not need to be increased in order to provide the desired gas pressure or flow to the patient.

In one embodiment of the present invention, pressure/flow generator 60 outputs a supply of breathing gas at a constant predetermined pressure or a constant predetermined flow during normal operation. Examples of such a device include a pressurized tank of breathing gas, a blower, piston, bellows compressor or concentrator operating at a constant rate. In this embodiment, pressure/flow generating system 48 includes a pressure/flow controller 64 associated with the constant pressure/flow generator to control the final pressure or flow of gas exiting the pressure/flow generating system, which is provided to the patient, so that the breathing gas can be supplied to the patient at a selectable pressure or selectable flow. Examples of suitable pressure/flow controllers include at least one valve, such as sleeve or poppet valve, that exhausts gas from the patient circuit as a method of controlling the pressure in the patient circuit. U.S. Pat. No. 5,694,923 to Hete et al., the contents of which are incorporated herein by reference, teaches a dual poppet valve system suitable for use as pressure/flow controller 64. Pressure/flow controller 64 operates under the control of a controller 66, which is preferably a processor that receives data and provides a control signal to pressure/flow controller 64 based thereon.

In an alternative embodiment of the present invention, pressure/flow controller 64 is incorporated into the pressure/flow generator 60 in the form of a variable speed motor that drives the blower to cause the pressure/flow generator to output the supply of breathing gas at the selectable pressure or selectable flow directly, i.e., without the need for additional pressure or flow control elements in the patient circuit.

In this embodiment, controller 66 controls the speed of the motor to control the pressure or flow of breathing gas output by pressure/flow generating system 48.

The exemplary embodiment of the present invention includes a flow transducer 68 that outputs a signal indicative of the flow characteristic of the supply of breathing gas within patient interface assembly 52, and, hence, within the airway of the patient. Flow transducer is typically coupled to patient interface assembly 52, including being connected along any portion of the flexible conduit 54 and/or at the patient interface device 56, to measure the flow or pressure of gas therein. Flow transducer 68 measures either flow of breathing gas to the patient using a mass flow sensor, for example, or the pressure of breathing gas in conduit 54 using a pneumatach device, for example, to determined the flow characteristics of the breathing gas within the conduit. The signal from flow transducer 68 is fed to controller 66, which uses this information to control pressure/flow controller 64 and/or pressure/flow generator 60 to ensure that pressure/flow generating system 48 outputs the flow of breathing gas to the patient at the selected pressure or flow rate.

In its simplest form, breathing gas delivery system 46 is a CPAP device that delivers a continuous flow of breathing gas to the patient. The term "continuous" used herein means that the pressure or flow rate does not vary based on the patient's inspiratory or expiratory phase of the breathing cycle. It is to be understood, that a "continuous" flow or pressure can vary based on the ramp function discussed above, but not based on the particular cycle or phase of the patient's respiratory cycle. The pressure or flow of breathing gas output by breathing gas delivery system 46 to the patient is selectable, for example to provide a pressure ramp, between a range of values. An example, of the output from such a breathing gas delivery system, when operating in the ramp cycle, is shown in FIG. 3.

In this embodiment, a physiological characteristic of the patient indicative of respiration is the change in flow in conduit 54 induced by the patient's respiratory efforts. In an exemplary embodiment of the present invention, this change in flow is detected by flow transducer 68. Based on the output of flow transducer 68, controller 66 can discern each respiratory cycle of the patient to maintain a running count of the number of respiratory cycles that have elapsed over a given period of time. It is to be understood, however, that there are other methods for detecting the change in flow in conduit 54 induced by the patient's respiratory efforts other than flow transducer 68. For example, as discussed above, it is known that the power provided to a motor driving the blower in the pressure/flow generator varies with changes in the flow of breathing gas in conduit 54. These changes in the motor's operating characteristics resulting from the patient's breathing into conduit 54 can be detected and used to identify the occurrence of the patient's respiratory cycles.

The present invention also contemplates that an external respiratory sensor 70, such as those discussed above with respect to respiratory cycle monitoring system 36 in FIG. 1, can be used, either alone or in conjunction with flow transducer 68 and/or a motor operating characteristic monitoring system, to detect the patient's respiratory cycles. It is to be understood that if flow transducer 68 is not used to detect patient respiration or to provide a feedback to control the pressure or flow provided by the pressure/flow generating system to the patient, the flow transducer can be eliminated, thereby reducing the cost and complexity of the breathing gas delivery system.

Figure 5:
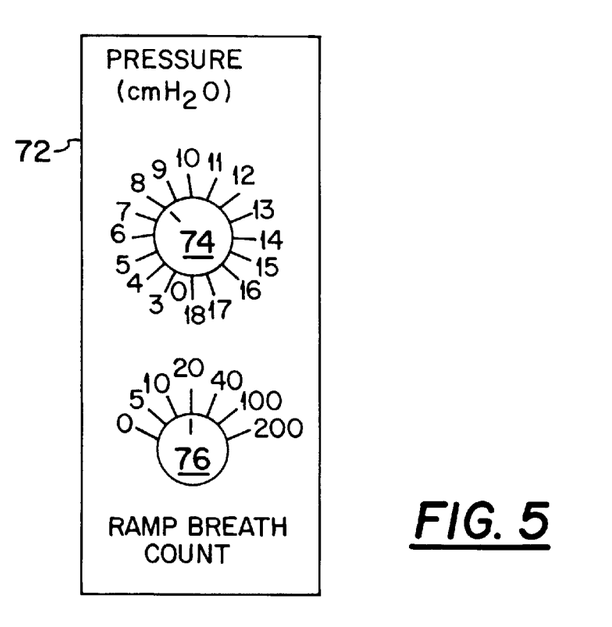
FIG. 5 illustrates pressure and ramp controls for use with the pressure support system of FIG. 4.

Breathing gas delivery system 46 includes a ramp control 72 to allow the user to select the desired parameters, such as respiratory cycle count R, for the ramp function. An exemplary embodiment of a suitable ramp control 72 that is provided on the housing for the breathing gas delivery system is shown in FIG. 5. Ramp control 72 includes a pressure dial 74 and a ramp breath count dial 76. Pressure dial 74 is used to set the maximum pressure $T_2$, which is typically prescribed by a physician. Of course, various lockout device can be employed to prevent the patient from adjusting the maximum pressure $T_2$ beyond or below the prescribed level. Ramp breath count dial 76 sets the number of respiratory cycles R for the ramp function. The present invention contemplates that controller 66, upon receiving this information, calculates the pressure increment $\Delta t$ need to achieve the desired ramp. For example, suppose that the initial CPAP pressure is set to 5 cmH$_2$O and the prescribed CPAP pressure is set to 15 cmH$_2$O and that a linear ramp function is to be used, i.e., $\Delta t$ remains constant over the ramp duration. If the user inputs the desired ramp breath count as 5 breaths (respiratory cycles) for example, the controller determines the pressure increment as: prescribed pressure $(T_2)$–initial pressure $(T_1)$/ramp breath count R, and substituting in the exemplary numbers, the pressure increment is determined to be 15 cmH$_2$O–5 cmH$_2$O/5 breaths=2 cmH$_2$O/ breath. Thus, controller 66 causes pressure/flow controller 64 to alter the pressure output by pressure/flow generating system 48 by 2 cmH$_2$O per breath to provide the desired ramp function.

It is to be understood that the present invention also contemplates that the user can manually set other parameters of the ramp function, or these other functions can be set automatically by controller 66. For example, ramp control 72 can be used to set the pressure increment $\Delta t$ directly rather than having the controller calculate this value. In addition, the number of respiratory cycles r after which a pressure change is made can also be set. In addition, the ramp control can be used to set limits on the amount of the pressure increment $\Delta t$, the pressure increment cycle r, and the ramp breath count R. These limits can also be built into ramp control 72 and/or controller 66 so that it is impossible for the user to select values outside such limits or for the breathing gas delivery system to exceed these limits regardless of the control settings. Furthermore, although FIG. 5 illustrates ramp control 72 as being dials used to set the ramp function variables, it is to be understood that other suitable input devices, such as switches, buttons, a touch screen, or a keypad, can be used to provide the ramp function parameters. In addition, the present invention contemplates that a remote control 78 can be used in place of or in conjunction with ramp control 72 provided on the housing of the pressure/flow generating system so that the patient can control the ramp function from a remote location.

Of course, other conventional features that control the pressure or flow to a patient can be employed in breathing gas delivery system 46. For example, a reset function can be provided, which, once activated, causes the ramp pressure or flow to drop to a low level. Thereafter, a second ramp, which is typically of shorter duration than the first ramp, can be provided to cause the system to transition back to the operating pressure. Alternatively, the system can resume operating at the pressure it was at prior to actuation of the reset, once a short reset period has elapsed. The duration between the actuation of the reset and the re-initiation of pressure therapy, which is either the resumption of the previous treatment level or the initiation of another ramp function, can be controlled based on the respiratory cycle count of the patient or via a conventional timer.

The present invention contemplates that other conventional functions associated with pressure support therapies can be provided in the breathing gas delivery system of the present invention. Examples of such functions include an automatic ON/OFF feature where the system turns on when the patient interface is donned by the patient and turns off when it is removed; minimum system leakage assurance that provides a relative high pressure at the start of the treatment for a short duration (either timed or based on breath count) to allow the user to adjust the patient interface device to reduce leaks; and a therapy delay function that delays operation of the unit for some duration, which can be timed or based on breath count. These and other functions are described in U.S. Pat. No. 5,239,995; U.S. Pat. No. Re. 35,295; U.S. Pat. Nos. 5,492,113, 5,551,418; and 5,823,187 all to Estes et al., the contents of which are incorporated herein by reference, and in U.S. Pat. No. 5,117,819 to Servidio et al., the contents of which is also incorporated herein by reference. In all of these various operating techniques, the present invention contemplates that where a period of time must be measured or must elapse before and action is taken, this period of time can be set or measured based on the patient's respiratory cycle count, rather than based on a timer, which can be insensitive to the particular respiratory characteristics of the patient.

The present invention also contemplates that breathing gas delivery system 46, in another embodiment of the present invention, is a bi-level system that delivers a different pressure or flow to the patient depending on whether the patient is in the inspiratory or expiratory phase of the respiratory cycle. During the inspiratory phase, an inspiratory positive airway pressure (IPAP) is provided to the patient, which is normally higher than during the expiratory phase, in which an expiratory positive airway pressure (EPAP) is provided to the patient. In this embodiment, controller 66 detects changes between the patient's inspiratory and expiratory phases and controls the pressure or flow provided to the patient accordingly. U.S. Pat. Nos. 5,148,802 and 5,433,193 both to Sanders et al., the content of which are incorporated herein by reference, and in U.S. Pat. No. 5,239,995; Re. U.S. Pat. No. 35,295; U.S. Pat. Nos. 5,492, 113, 5,551,418; and 5,823,187 all to Estes et al., the contents of which are again incorporated herein by reference, teach detecting changes between inspiration and expiration and controlling the pressure or flow to the patient based thereon, especially in a system that includes leaks, such as the leak through exhaust port 58.

Figure 6:
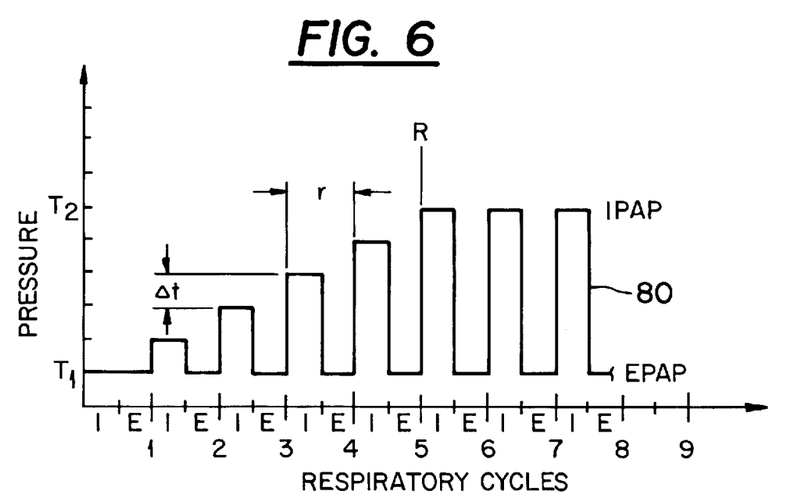
FIG. 6 is a waveform illustrating an example of bi-level pressure provided to the patient by the pressure support device schematically illustrated in FIG. 4.

In this bi-level embodiment, the present invention contemplates adjusting the IPAP and EPAP levels independently according to a respiratory cycle count ramp function. FIGS. 6 and 7A–7D illustrate example of the use of the respiratory cycle based ramp function to control the IPAP and/or EPAP levels. More specifically, FIG. 6 illustrates a pressure curve 80 in which the IPAP level transitions from a first predetermined minimum pressure $T_1$ to a prescribed pressure $T_2$ over a first predetermined number $R_1$ of respiratory cycles. The incremental increase $\Delta t$ in the IPAP level occurs every r respiratory cycles, where r=1. The EPAP level in FIG. 6 remains constant. It can be appreciated that there are a number of similarities in controlling the single pressure in a CPAP system, as shown, for example, in FIGS. 3 and 4, and controlling the dual IPAP and EPAP levels independently, as shown in FIG. 6. In a CPAP system, such as that of FIGS. 3 and 4, the parameters $T_1$, $T_2$, $\Delta t$, $R_1$, and r are set for the one output pressure or flow from the system. In a bi-level system, however, these parameters, $T_1$, $T_2$, $\Delta t$, $R_1$, and r, must be set for the IPAP and EPAP independently.

Figure 7A:
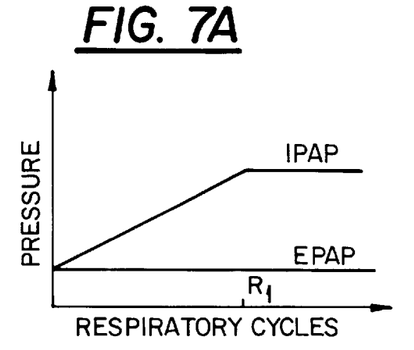
FIGS. 7A–7D are waveforms illustrating various IPAP and EPAP ramp functions.
Figure 7B:
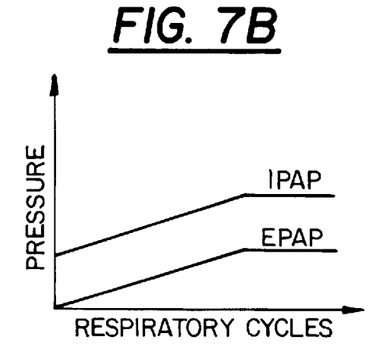
Figure 7C:
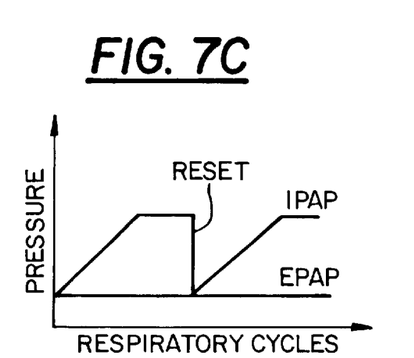
Figure 7D:
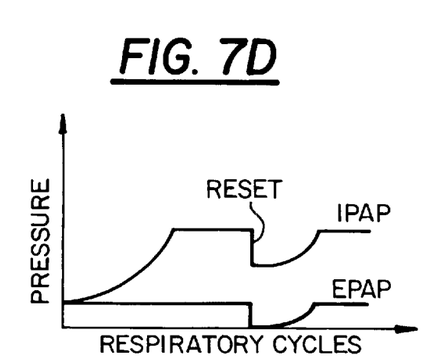

While it is not possible to illustrate exhaustively all possible scenarios for the various ramping operations between the IPAP and EPAP levels, FIGS. 7A–7D are provided to illustrate exemplary variations for the respiratory cycle count ramp functions that can be achieved based on how the parameters $T_1$, $T_2$, $\Delta t$, $R_1$, and r, are set for IPAP and EPAP. FIG. 7A illustrated the pressure ramp function shown in FIG. 6. Of course, the conventional functions associated with pressure support therapies, such as reset, auto on/off, therapy delay, and the like can be provided in the bi-level breathing gas delivery system of the present invention.

In many bi-level ventilation systems, the patient's own respiratory effort is monitored and used to control the triggering between providing IPAP and EPAP. However, it is also known to trigger changes in patient ventilation between expiration and inspiration based on the elapse of time. For example, if patient does not breathe for a certain period of time, the ventilator can be programmed to initiate a respiratory cycle. Conventional ventilators can also provide ventilation to a patient that is purely based on time, so that the patient gets a respiration every 5–10 seconds, for example, regardless of patient effort. This timed mode of ventilation is used primarily when the patient is unable to breathe on their own. The present invention contemplates that the respiratory cycle monitor considers this machine-generated respiratory cycle as a patient respiratory cycle for the purposes of counting the number of respiratory cycles.

The present invention further contemplates that the respiratory cycle based control of the treatment level being provided to the patient can be applied to other modes of ventilating a patient. For example, U.S. Pat. Nos. 5,535,738 and 5,794,615 both to Estes et al., the contents of which are incorporated herein by reference, disclose a device and method of providing a pressure support therapy to a patient in which the pressure support provided to the patient is a function of the patient flow rate. This mode of ventilating a patient is commonly referred to as proportional positive airway pressure (PPAP) therapy. According to this technique, the pressure delivered to the patient is described as:

$$P_{delivered} = P_{base} + \text{Gain} * \text{Flow}, \quad (1)$$

where $P_{delivered}$ is the pressure delivered to the patient interface; $P_{base}$ is the base line pressure (greater than or equal to zero and conceptually equal to EPAP); Flow is the estimated patient flow rate determined by the flow transducer; and Gain is a constant used to augment the pressure delivered to the patient based on the flow rate.

In another embodiment of the invention described in U.S. Pat. Nos. 5,535,738 and 5,794,615, the pressure output is described according to the following functions:

$$P_{inhalation} = P_{base} + \text{Gain}_{Insp} * \text{Flow}, \quad (2)$$

and $$P_{exhalation} = P_{base} + \text{Gain}_{Exp} * \text{Flow}, \quad (3)$$

where $P_{inhalation}$ it the pressured delivered to the patient during inhalation, $\text{Gain}_{Insp}$ is the constant used during inspiration (positive flow) to boost pressure based on the flow rate, $P_{exhalation}$ is the pressure delivered during exhalation, and $\text{Gain}_{Exp}$ is the constant used during exhalation (negative flow) to reduce pressure based on the flow rate.

Similar to previous embodiments of the invention, the present embodiment contemplates varying one or more of the following: base line pressure $P_{base}$, Gain, $\text{Gain}_{Insp}$, and/or $\text{Gain}_{Exp}$, between two predetermined values $T_1$ and $T_2$ over a first predetermined number of patient respiratory cycles R. In addition, the present embodiment contemplates varying one or more of these items by an incremental amount $\Delta t$ each time a second predetermined number r of respiratory cycles has elapsed so that the flow or pressure support provided to the patient changes as the patient's respiratory cycle count increases. It can be appreciated that $P_{base}$, Gain, $\text{Gain}_{Insp}$ and/or $\text{Gain}_{Exp}$ can be varied in any combination or independently over the first predetermined number of patient respiratory cycles R depending on the desired ramp function to be provided. It should be further noted that these items can be varied in an increasing or decreasing manner. For example, there may be situations in which it may be beneficial to decrease the amount of pressure assist being delivered to the patient so that the patient can assume more of the work of breathing the longer they breathe on the ventilator.

Figure 8:
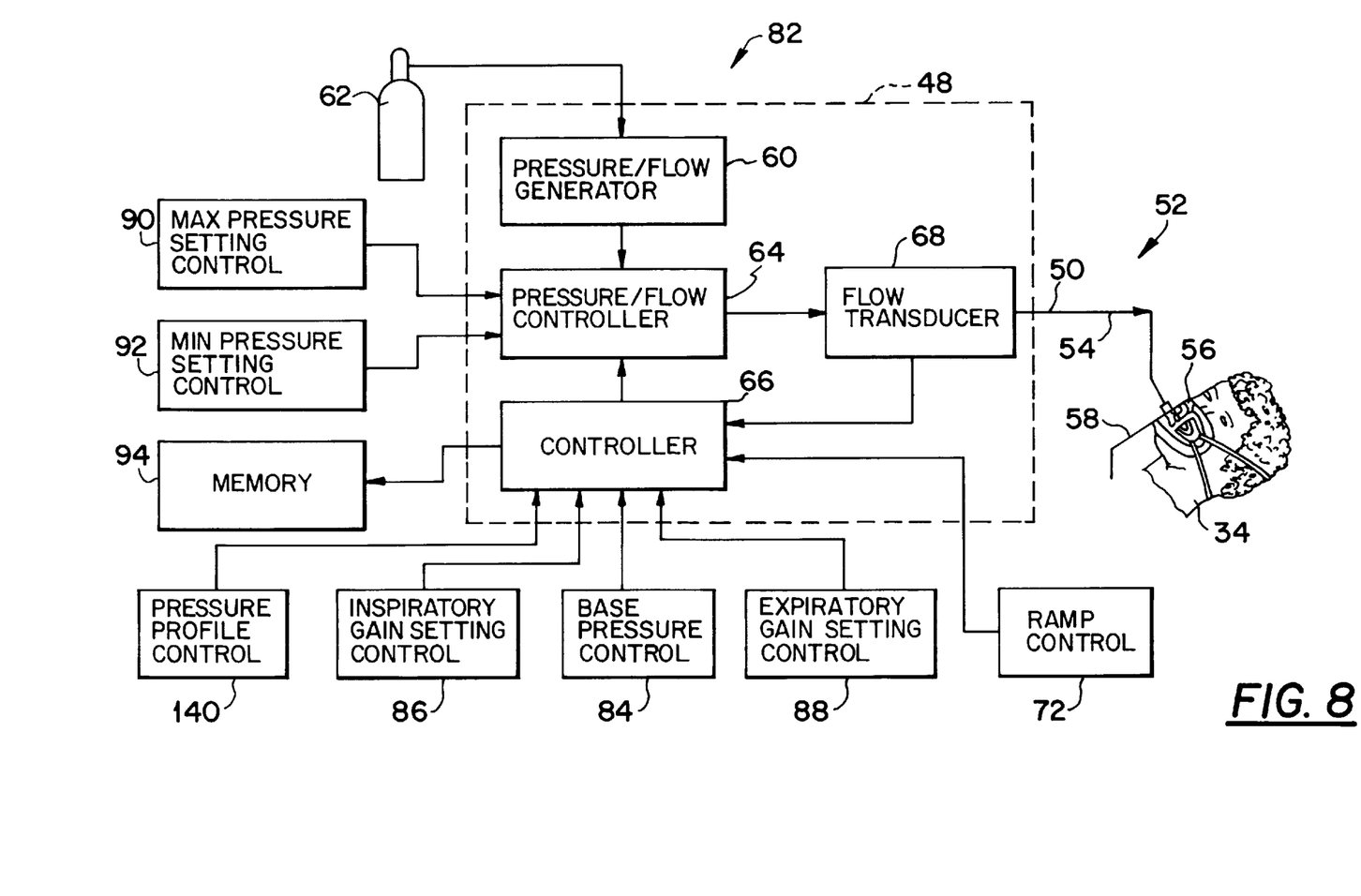
FIG. 8 is a schematic diagram of another pressure support device as the patient treatment system.

FIG. 8 illustrates a breathing gas delivery system 82 according to this embodiment of the invention. The basic components of the breathing gas delivery system are the same as those discussed above with respect to FIG. 4. However, in the embodiment illustrated in FIG. 8, controller 66 causes pressure/flow controller 64 to output a pressure to the patient in accordance with above-described equations (1)–(3) so that the output pressure varies over each respiratory cycle. In the device of FIG. 4, the output pressure or flow remains constant over the entire respiratory cycle in the case of CPAP and over the inspiratory phase (IPAP) or expiratory phase (EPAP) in the case of the bi-level pressure support system. In addition, breathing gas delivery system 82 includes a base pressure control 84 that sets base pressure $P_{base}$, an inspiratory gain setting control 86 that sets inspiratory gain $\text{Gain}_{Insp}$, and an expiratory gain setting control 88 that sets expiratory gain $\text{Gain}_{Exp}$. Controls 84–88 can be any suitable input/output device for providing the necessary data to controller 66. Of course, if only one gain is used for both inspiration and expiration, as is the case in above equation (1), gain setting control 86 or 88 can be eliminated.

Breathing gas delivery system 82 also desirably includes a safety circuit, preferably comprising an adjustable maximum pressure setting control 90 and an adjustable minimum pressure setting control 92 operatively connected to pressure/flow controller 64. The safety circuit allows the manufacturer, the patient or his overseeing health care professional to selectively establish minimum and maximum system output pressures below and above which the system will not dispense pressurized gas. The safety circuit functions differently than the pressure controls which determine, for instance, the CPAP prescription pressure or the IPAP and EPAP prescription pressures used in bi-level PAP therapy. That is, instead of establishing lower and upper prescription pressures to be administered during normal usage of the apparatus, the maximum and minimum pressure setting controls 90 and 92 set absolute minimum and maximum fail-safe output pressure limits which are not to be exceeded, thereby maximizing the safety of the pressure support system.

Breathing gas delivery system 82 also has the capacity to measure and store in a memory 94 the following parameters: tidal volume, inspiratory time, expiratory time, peak pressure, peak flow, oxygen saturation (as a signal input from an external source), pleural pressure (as a signal input from an outside source), mask pressure, estimated leakage, and system parameters, e.g., $P_{base}$, $\text{Gain}_{Insp}$, $\text{Gain}_{Exp}$, IPAP and EPAP. It is to be understood that this list is not exclusive; other parameters can be stored in memory 94.

Figures 9A, 9B:
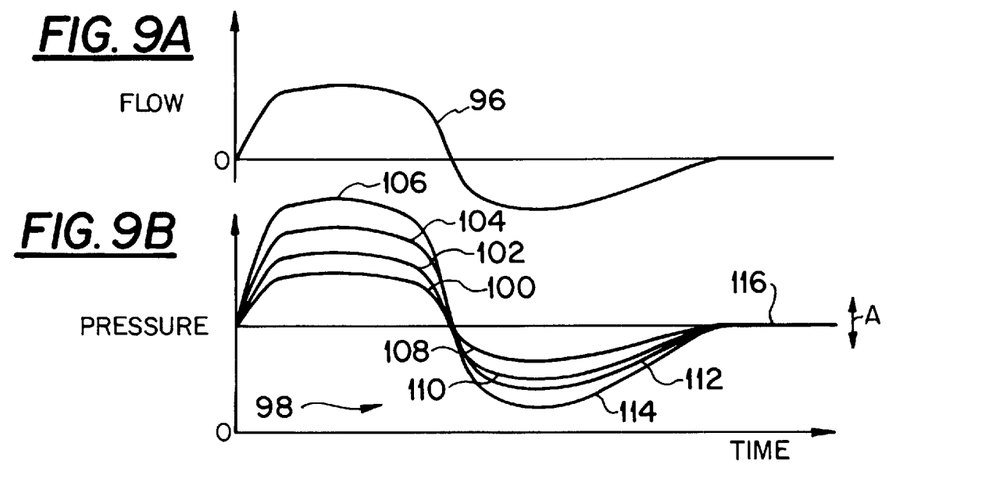
FIGS. 9A–9B, 10A–10B and 11A–11B illustrate exemplary output flow and pressure curves that can be provided by the pressure support device of FIG. 8 and further show how the pressure provided to the patient can vary over a number of patient breaths.

FIGS. 9A and 9B illustrate a flow curve 96 and pressure curves 98 that can be provided by the above-described device shown in FIG. 8 as the $\text{Gain}_{Insp}$ and $\text{Gain}_{Exp}$ are adjusted during successive respiratory cycles. Pressure curve 100 illustrates $\text{Gain}_{Insp}$ set to a first predetermined level. Pressure curves 102, 104 and 106 illustrate how the inspiratory portion of the pressure curve changes as a result of increasing $\text{Gain}_{Insp}$ over successive respiratory cycles. Similarly, pressure curve 108 illustrates $\text{Gain}_{Exp}$ set to a first predetermined level, and pressure curves 110, 112 and 114 illustrate how the inspiratory portion of the pressure curve changes as a result of increasing $\text{Gain}_{Exp}$ over successive respiratory cycles. It should also be noted that base pressure 116 can be increased or decreased, as indicated by arrow A, in addition to or in place of the changes in $\text{Gain}_{Insp}$ and $\text{Gain}_{Exp}$ over successive respiratory cycles.

Additional embodiments for providing PPAP to a patient include providing PPAP in combination with CPAP or in combination with bi-level pressure support so that a portion of the pressure profile is provided to the patient in accordance with a PPAP technique and another portion of the pressure profile is provided in accordance with a CPAP technique. The present invention contemplates controlling that the PPAP portion of the pressure output, which is provided in accordance with either equation (1), (2) or (3), according to a respiratory cycle count based ramp function as discussed above with respect to FIG. 8 and controlling the CPAP or bi-level portion of the pressure output as discussed above with respect to FIG. 4. Of course, in the bi-level mode, controller 66 includes the necessary circuits and/or programming to effect the bi-level pressure control, including leak compensation.

Figures 10A, 10B:
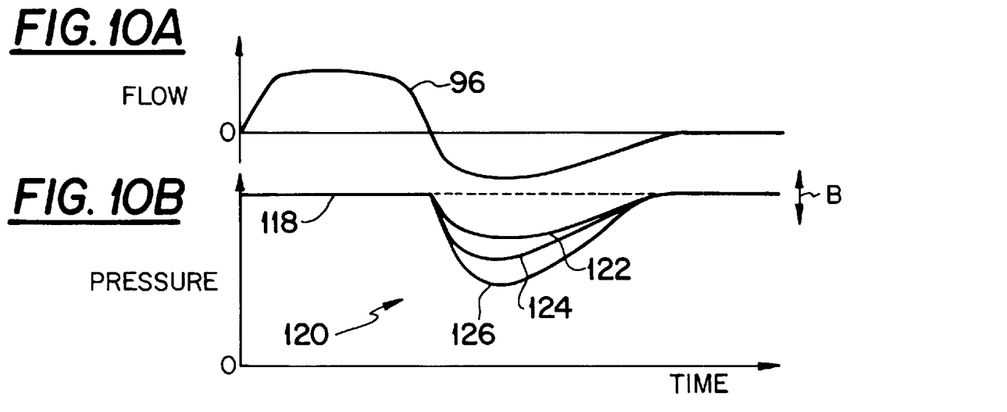

FIGS. 10A and 10B are exemplary flow and pressure curves, respectively, showing an example of the use of PPAP control, which is provided in accordance with either equation (1), (2) OR (3), in conjunction with CPAP 118. In this embodiment, PPAP control is only used during the expiratory phase. It can be appreciated, however, that PPAP control can be used at other portions of the respiratory cycle, with CPAP control being used whenever PPAP control is not applied. Using PPAP control only during the expiratory phase results in a decrease in pressure provided to the patient as illustrated by pressure curves 120 during the expiratory phase. A result similar to that shown in FIGS. 10A and 10B is achieved if $Gain_{Insp}$ in equation (2) is set to zero, with $P_{base}$ being the CPAP pressure. Pressure curve 122 illustrates $Gain_{Exp}$ set to a first predetermined level, and pressure curves 124 and 126 illustrate how the expiratory portion of the pressure curve changes as a result of increasing $Gain_{Exp}$ over successive respiratory cycles. CPAP level 118 can be increased or decreased, as indicated by arrow B, over successive respiratory cycles in addition to or in place of the changes in $Gain_{Insp}$ and $Gain_{Exp}$.

Figures 11A, 11B:
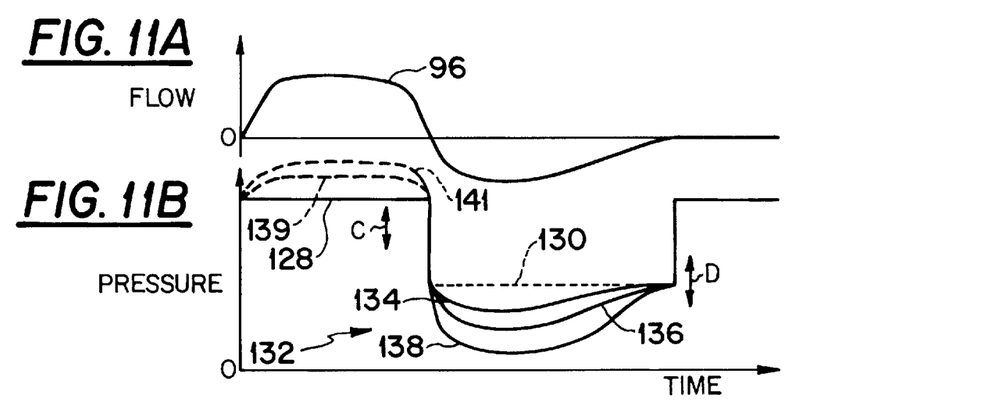

FIGS. 11A and 11B are flow and pressure curves, respectively, showing an example of the use of PPAP control, which is provided in accordance with either equation (1), (2) OR (3), with bi-level pressure control. As shown in FIG. 11B, an IPAP 128 is provided during inspiration and an EPAP 130 is provided during expiration. In this embodiment, PPAP control is only used during the expiratory phase. It can be appreciated, however, that PPAP control can also be used during the inspiratory phase or during both phases in combination with the PPAP control. Providing PPAP control in combination with bi-level control during the expiratory phase results in a decrease in pressure provided to the patient as illustrated by pressure curves 132 during the expiratory phase. Pressure curve 134 illustrates $Gain_{Exp}$ set to a first predetermined level, and pressure curves 136 and 138 illustrate how the expiratory portion of the pressure curve changes as a result of increasing $Gain_{Exp}$ over successive respiratory cycles. IPAP level 128 and EPAP level 130 can be increased or decreased, as indicated by arrows C and D, respectively, over successive respiratory cycles in addition to or in place of the changes in $Gain_{Insp}$ and $Gain_{Exp}$. Dashed lines 139 and 141 illustrate how the pressure curve would look during inspiration if PPAP control is used in combination with IPAP during the inspiratory phase. $Gain_{Insp}$ in pressure curve 141 is greater than $Gain_{Insp}$ in pressure curve 139.

It is also known to use PPAP in conjunction with a predetermined pressure profile so that a portion of the pressure output follows a preset pressure profile. FIG. 8 illustrates a pressure profile control 140 that is used to actuate and set the pressure profile to be used in conjunction with the PPAP pressure. The PPAP portion of the pressure output, which is provided in accordance with equation (1), (2) OR (3), can be controlled according to a respiratory cycle count based ramp function as discussed above with respect to FIG. 8, with the predetermined pressure remaining unchanged. Alternatively, or in addition to modifying the PPAP portion on a breath count basis, different pressure profiles can be selected following the elapse of a predetermined number of respiratory cycles to allow the profile portion of the pressure curve to vary as the patient breathes.

The present invention also contemplates that the respiratory cycle, i.e., breath count, based control of the treatment level provided to the patient can be applied to the mode of ventilating a patient taught by U.S. Pat. Nos. 5,044,362 and 5,107,830 both to Younes et al., the contents of which are incorporated herein by reference. These patents disclose a device and method of providing a pressure support therapy to a patient in which the pressure support provided to the patient is a function of the patient effort, which is commonly referred to as proportional assist ventilation (PAV).

According to this technique, the pressure delivered by the ventilator to the patient is determined based on a product of a first gain and a signal indicative of a rate of flow of breathing gas provided to such a patient in combination with a product of a second gain and signal indicative of a volume of breathing gas provided to the patient. This relationship is summarized as follows:

$$P_{mask} = FA*\dot{V} + VA*V, \tag{4}$$

where $P_{mask}$ is the pressure at the patient interface device, such as the patient's mask, FA is a flow assist multiplier, $\dot{V}$ is the instantaneous flow of gas to the patient, VA is a volume assist multiplier, and V is the instantaneous volume of gas to the patient.

The present invention contemplates adjusting the flow assist FA and/or the volume assist VA from a first predetermined level $T_1$ to a second predetermined level $T_2$ over a first predetermined number of respiratory cycles R by a predetermined $\Delta t$ amount over a second predetermined number r of respiratory cycles of such a patient. It is to be understood that each gain can be adjusted independently. Thus, the level PAV assist can vary as a function of the number of breathing taken by the patient.

In a slight variant of the above-described PAV mode, another embodiment of the present invention contemplates providing pressure support to a patient according to the following equation:

$$P_{mask} = \% \, Set(FA*\dot{V} + VA*V) + EPAP, \tag{5}$$

where % Set is a common multiplier or scaling factor applied to both $FA*\dot{V}$ and $VA*V$, and EPAP is the expiratory positive airway pressure.

This embodiment contemplates modifying equation (5) over a number of patient breaths by altering one or more terms in this equation on a breath count basis. Modifying one or more terms in equation (5) can be accomplished, for example, by altering a multiplier α an incremental amount Δα over a range of values, such as from $α_0$ to 1, over R respiratory cycles. The multiplier α being changed every predetermined number r of breaths can be applied to any term or any combination of terms in equation (5) to achieve a variety of different pressure modifications over a number of patient breathing. The following equations are examples of where the multiplier α, which varies based on the number of respiratory cycles of the patient, can be inserted into equation (5):

$$P_{mask} = α(\% \, Set(FA*\dot{V} + VA*V) + EPAP), \tag{6}$$

$$P_{mask} = α*\% \, Set(FA*\dot{V} + VA*V) + EPAP), \tag{7}$$

$$P_{mask} = \% \, Set(αFA*\dot{V} + VA*V) + EPAP), \tag{8}$$

$$P_{mask} = \% \, Set(FA*\dot{V} + αVA*V) + EPAP), \tag{9}$$

$$P_{mask} = Set(FA*\dot{V} + VA*V) + αEPAP), \tag{10}$$

As noted above, the multiplier α can be applied to more than one term in equation (5) as well as any combination of terms.

Figure 12:
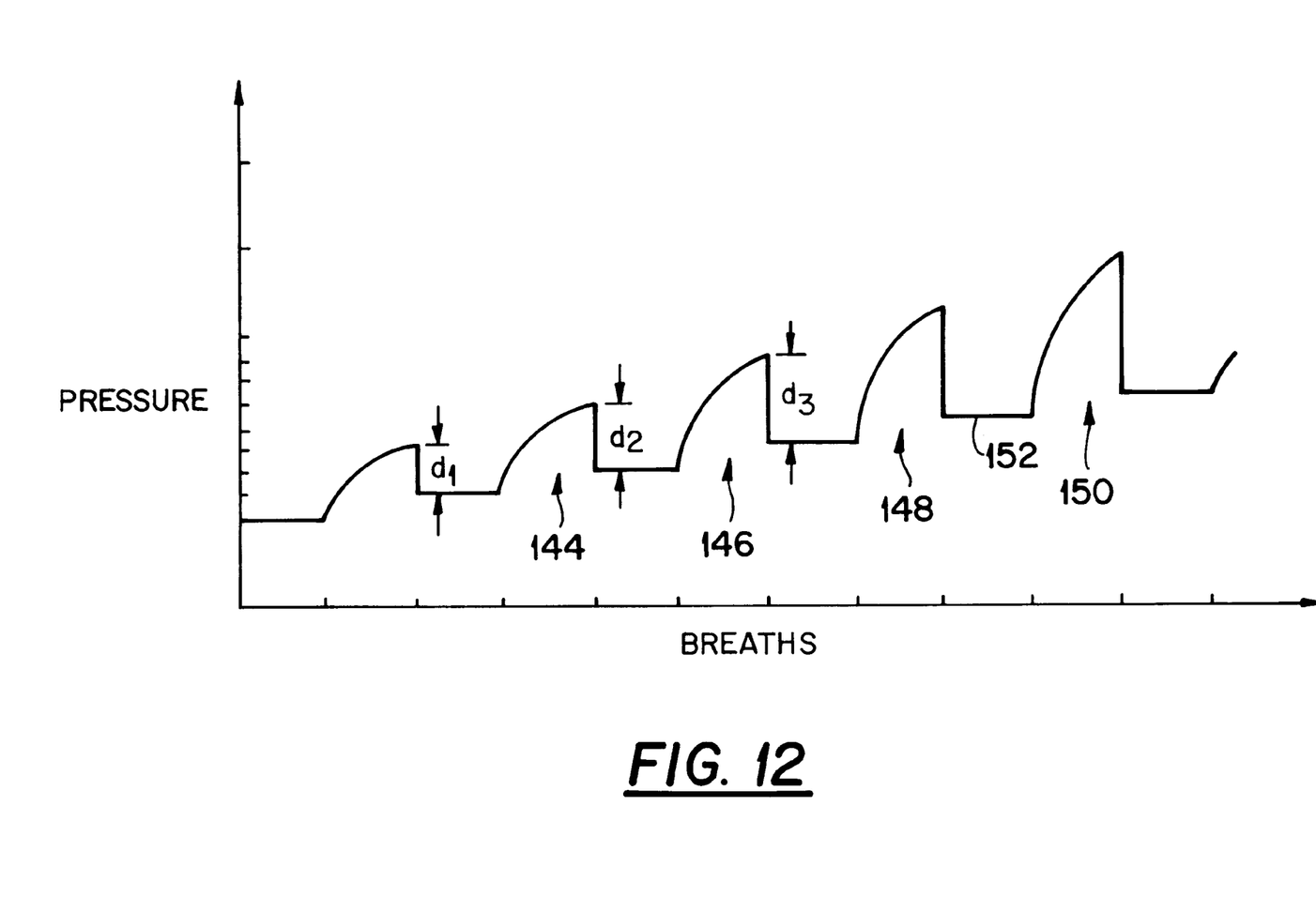
FIG. 12 is a pressure curve providing according to a further embodiment of the present invention also showing how the pressure provided to the patient can vary over a number of patient breaths.

FIG. 12 is a pressure curve 142 illustrating how the pressure provided to the patient can vary on a breath count basis. More specifically, FIG. 12 illustrates how the pressure provided to the patient according to equation (6) varies if α is incremented on each breath. Because the breath count variable multiplier α is applied to each term in equation (6), the general shape of curve 142 remains the same as α is incremented after each breath. However, the overall size of curve 142 increases in later breaths 144, 146, 148, 150 as a result of altering a after each breath. For example, in FIG. 12, the distance $d_1$, $d_2$, and $d_3$ are increased in subsequent breaths. In addition, the EPAP level 152 also increases in later breaths, because, in this situation, a is applied to the EPAP level.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient treatment system comprising:
   treatment means for providing a therapeutic treatment to a patient at variable treatment levels;
   respiratory cycle monitoring means for detecting a respiratory cycle of a patient; and
   treatment modifying means for changing said treatment level from a first predetermined treatment level to a second predetermined treatment level over a first predetermined number of respiratory cycles of such a patient by adjusting an output of said treatment means a first predetermined amount over a second predetermined number of respiratory cycles of such a patient.

2. A patient treatment system according to claim 1, wherein:
   (a) said treatment means is a system for delivering a flow of breathing gas to a patient,
   (b) said respiratory cycle monitoring means is a sensor adapted to monitor a physiological characteristic of such a patient indicative of a respiratory cycle, and
   (c) said treatment modifying means causes said system for delivering breathing gas to transition from one of a first predetermined pressure and a first predetermined flow to one of a second predetermined pressure and a second predetermined flow over said first predetermined number of respiratory cycles of such a patient by adjusting an output of said system for delivering breathing gas by said first predetermined amount over said second predetermined number of respiratory cycles of such a patient.

3. A patient treatment system according to claim 2, wherein said first predetermined pressure is a minimum pressure, said first predetermined flow is a minimum flow, said second predetermined pressure is a maximum pressure, said second predetermined flow is a maximum flow.

4. A patient treatment system according to claim 2, wherein said first predetermined pressure is a maximum pressure, said first predetermined flow is a maximum flow, said second predetermined pressure is a minimum pressure, said second predetermined flow is a minimum flow.

5. A patient treatment system according to claim 2, wherein:
   (a) said system for delivering a flow of breathing gas to a patient comprises:
      a pressure/flow generating means for supplying breathing gas at one of a selectable pressure and a selectable flow, and
      a patient interface assembly operatively coupled to said pressure/flow generating means to communicate said supply of breathing gas from said pressure/flow generating means to an airway of a patient,
   (b) said respiratory cycle monitoring means is a flow/pressure sensing system adapted to detect one of a flow of gas and a pressure of gas in said patient interface assembly and to output a signal indicative thereof, and
   (c) said treatment modifying means includes a controller operatively coupled to said system for delivering breathing gas and to said flow sensing system for incrementally changing one of a pressure and a flow output by said system for delivering a flow of breathing gas based on said signal from said flow/pressure sensing system over at least one respiratory cycle of such a patient.

6. A patient treatment system according to claim 5, wherein said pressure/flow generating means includes:
   a constant pressure/flow generator that outputs one of a constant predetermined pressure and a constant predetermined flow during normal operation, and
   a breathing gas pressure/flow controller operatively coupled to said constant pressure/flow generator and said controller, wherein said breathing gas pressure/flow controller varies one of said constant predetermined pressure and said constant predetermined flow output from said constant pressure/flow generator based on an output from said controller to provide one of said selectable pressure and said selectable flow.

7. A patient treatment system according to claim 6, wherein said constant pressure/flow generator is selected from the group consisting of: a pressurized tank of breathing gas, a blower, a piston, a bellows, a compressor, and a concentrator.

8. A patient treatment system according to claim 5, wherein said pressure/flow generating means is a variable pressure/flow generator that outputs one of (1) a variable pressure as said selectable pressure and (2) a variable flow as said selectable flow during normal operation based on an output of said controller.

9. A patient treatment system according to claim 8, wherein said variable pressure/flow generator comprises a blower and a variable speed motor operatively coupled to said blower and to said controller, wherein a speed of said variable speed motor is controlled based on said output from said controller.

10. A patient treatment system according to claim 5, wherein said patient interface assembly includes:
   a conduit having a first end coupled to said pressure/flow generating means and a second end; and
   a patient interface device coupled to said second end of said conduit for communicating a supply of breathing gas carried by said conduit to an airway of a patient.

11. A patient treatment system according to claim 5, wherein said controller determines an inspiratory phase and an expiratory phase of said respiratory cycle based on an output of said respiratory cycle monitoring means and independently adjusts said system for delivering a flow of breathing gas during said inspiratory phase and said expiratory phase so that, in at least one of said inspiratory phase and said expiratory phase, said system for delivering a flow of breathing gas transitions from one of said first predetermined pressure and said first predetermined flow to one of said second predetermined pressure and said second predetermined flow over said first predetermined number of respiratory cycles of such a patient by said first predetermined amount over said second predetermined number of respiratory cycles of such a patient.

12. A patient treatment system according to claim 1, wherein said respiratory cycle monitoring means is selected from the group consisting of: (1) an acoustic system adapted to detect sounds associated with a patient's respiration, (2) a motion detecting system adapted to detect movement of a patient associated with a patient's respiration, (3) a temperature detecting system adapted to detect temperature variations associated with a patient's respiration, (4) an electrical signal sensing system adapted to detect electrical activity of a patient associated with a patient's respiration, (5) a pressure sensing system associated with a patient's respiratory system to detect pressure variations induced by patient respiration, (6) a flow sensing system associated with a patient's respiratory system to detect flow variations induced by patient respiration, and (7) a treatment means monitor that detects changes in operation of said treatment means resulting from patient respiration.

13. A patient treatment system according to claim 1, wherein
    (a) said treatment system is a system for providing medication to a patient at variable dosage rates,
    (b) said respiratory cycle monitoring means is a sensor adapted to monitor a physiological characteristic of such a patient indicative of a respiratory cycle, and
    (c) said treatment modifying means causes said system for providing medication to transition from a first predetermined dosage rate to a second predetermined dosage rate over said first predetermined number of respiratory cycles of such a patient by adjusting an output of said system for providing medication by said first predetermined amount over said second predetermined number of respiratory cycles of such a patient.

14. A patient treatment system according to claim 1, wherein:
    (a) said treatment means comprises:
        a gas flow generator adapted to generate a flow of breathing gas,
        a patient interface operatively associated with said gas flow generator to communicate said flow of breathing gas to an airway of a patient,
        a pressure/flow controller associated with at least one of said gas flow generator and said patient interface to control one of a pressure and a flow of breathing gas provided to an airway of such a patient,
        first means for establishing a first gain, and
        control means, operatively coupled to said pressure/flow controller and said first means for establishing said first gain, for controlling one of said pressure and said flow of breathing gas based on a fluid characteristic signal and said first gain;
    (b) wherein said respiratory cycle monitoring means comprises a sensor adapted to detect at least one fluid characteristic associated with a flow of gas within said patient interface and to provide said fluid characteristic signal that corresponds to said characteristic; and
    (c) wherein said treatment modifying means causes said control means to adjust said first gain from a first predetermined level to a second predetermined level over said first predetermined number of respiratory cycles of such a patient by said first predetermined amount over said second predetermined number of respiratory cycles of such a patient.

15. A patient treatment system according to claim 14, wherein said at least one fluid characteristic is a rate of said flow of breathing gas within said patient interface.

16. A patient treatment system according to claim 14, wherein said treatment means further comprises a second means for establishing a second gain, said control means applying said first gain to a first fluid characteristic signal output said sensor, said first fluid characteristic signal corresponding to a fluid characteristic indicative of inspiration, and applying said second gain to a second fluid characteristic signal output by said sensor, said second fluid characteristic signal corresponding to a fluid characteristic indicative of expiration, and wherein said treatment modifying means also causes said control means to adjust said second gain from a third predetermined level to a fourth predetermined level over a third predetermined number of respiratory cycles of such a patient by a second predetermined amount over a fourth predetermined number of respiratory cycles of such a patient.

17. A patient treatment system according to claim 14, wherein said control means also controls one of said pressure and said flow of breathing gas based on one of a base pressure and a base flow rate in addition to said controlling said flow of breathing gas based on said first gain and said fluid characteristic signal, and wherein said treatment modifying means causes said control means to adjust one of said base pressure and said base flow rate from a first predetermined level to a second predetermined level over a third predetermined number of respiratory cycles of such a patient by said predetermined amount over a fourth predetermined number of respiratory cycles of such a patient.

18. A patient treatment system according to claim 1, wherein
    (a) said treatment means comprises:
        a gas flow generator adapted to generate a flow of breathing gas,
        a patient interface operatively associated with said gas flow generator to communicate said flow of breathing gas to an airway of a patient,
        a pressure/flow controller associated with at least one of said gas flow generator and said patient interface to control one of a pressure and a flow of breathing gas provided to an airway of such a patient,
        first means for establishing a first gain and a second gain, and
        control means, operatively coupled to said pressure/flow controller and said first means for establishing said first gain and said second gain, for controlling one of said pressure and said flow of breathing gas;
    (b) wherein said respiratory cycle monitoring means comprises:
        (1) means for determining a rate of said flow of breathing gas provided to such a patient and to provide a first signal corresponding to said rate of said flow of breathing gas, and
        (2) means for determining a volume of breathing gas provided to such a patient and to provide a second signal corresponding to said volume, wherein said control means controls one of said pressure and said flow of breathing gas provided to a patient based on a first product of said first gain and said first signal in combination with a second product of said second gain and said second signal; and
    (c) wherein said treatment modifying means causes said control means to adjust at least one of said first gain and said second gain from a first predetermined level to a second predetermined level over said first predetermined number of respiratory cycles of such a patient by said predetermined amount over said second predetermined number of respiratory cycles of such a patient.

19. A patient treatment system according to claim 1, wherein:

(a) said treatment means comprises:
  a gas flow generator adapted to generate a flow of breathing gas,
  a patient interface operatively associated with said gas flow generator to communicate said flow of breathing gas to an airway of a patient,
  a pressure/flow controller associated with at least one of said gas flow generator and said patient interface to control one of a pressure and a flow of breathing gas provided to an airway of such a patient, and
  control means, operatively coupled to said pressure/flow controller for controlling one of said pressure and said flow of breathing gas provided to a patient based on a product of said fluid characteristic signal and a gain in combination with one of a base pressure and a base flow rate;
(b) wherein said respiratory cycle monitoring means comprises a sensor adapted to detect at least one fluid characteristic associated with a flow of gas within said patient interface and to transmit said signal corresponding to said characteristic; and
(c) wherein said treatment modifying means causes said control means to adjust one of said base pressure and said base flow rate from one of a first predetermined pressure level and a first predetermined flow rate to one of a second predetermined pressure level said a second predetermined flow rate over said first predetermined number of respiratory cycles of such a patient by said predetermined amount over said second predetermined number of respiratory cycles of such a patient.

20. A patient treatment system according to claim 1, further comprising means for adjusting at least one of said first predetermined level, said second predetermined level, said first predetermined number of respiratory cycles, said second predetermined number of respiratory cycles, and said predetermined amount to control how said treatment changes over a plurality of respiratory cycles of such a patient.

21. A method of treating a patient comprising:
  providing a therapeutic treatment to a patient at variable treatment levels;
  detecting a respiratory cycle of such a patient; and
  changing said treatment level from a first predetermined treatment level to a second predetermined treatment level over a first predetermined number of respiratory cycles of such a patient by adjusting a treatment level by a first predetermined amount over a second predetermined number of respiratory cycles of such a patient.

22. A method of treating a patient according to claim 21, wherein
  (a) said step of providing a therapeutic treatment includes delivering a flow breathing gas to a patient,
  (b) said detecting step includes monitoring a physiological characteristic of such a patient indicative of a respiratory cycle via a sensor, and
  (c) said step of changing said treatment level includes transitioning one of a pressure and a flow of said breathing gas from one of a first predetermined pressure and a first predetermined flow to one of a second predetermined pressure and a second predetermined flow over said first predetermined number of respiratory cycles of such a patient by adjusting one of a flow and a pressure of said breathing gas by said first predetermined amount over said second predetermined number of respiratory cycles of such a patient.

23. A method of treating a patient according to claim 22, wherein:
  (a) said step of delivering a breathing gas to a patient comprises:
    supplying breathing gas to a patient at one of a selectable pressure and a selectable flow, and
    communicating said supply of breathing gas to an airway of such a patient,
  (b) said monitoring step includes detecting one of a flow of breathing gas and a pressure of breathing gas and outputting a signal indicative thereof, and
  (c) said transitioning step includes incrementally changing one of a pressure and a flow of breathing gas provided in said breathing gas delivery step based on said signal.

24. A method of treating a patient according to claim 23, wherein said step of supplying breathing gas to a patient includes:
  generating one of a constant predetermined pressure and a constant predetermined flow;
  regulating one of said constant predetermined pressure and said constant predetermined flow to produce one of said selectable pressure and said selectable flow.

25. A method of treating a patient according to claim 23, wherein said step of supplying breathing gas to a patient includes:
  generating one of a variable pressure and a variable flow as an associated one of said selectable pressure and said selectable flow via a variable speed pressure/flow generating device; and
  controlling a speed of said variable speed pressure/flow generating device.

26. A method of treating a patient according to claim 23, wherein said monitoring step includes determining an inspiratory phase and an expiratory phase of said respiratory cycle based at least one of said detected flow and said detected pressure of breathing gas, and wherein said transitioning step includes independently adjusting one of said selectable pressure and said selectable flow of said breathing gas during said inspiratory phase and said expiratory phase so that in at least one of said inspiratory phase and said expiratory phase said supply of breathing gas transitions from one of said first predetermined pressure and said first predetermined flow to one of said second predetermined pressure and said second predetermined flow over said first predetermined number of respiratory cycles of such a patient by said first predetermined amount over said second predetermined number of respiratory cycles of such a patient.

27. A method of treating a patient according to claim 21, wherein
  (a) providing a therapeutic treatment includes providing a medication to a patient at variable dosage rates,
  (b) detecting a respiratory cycle includes detecting, via a sensor associated with a patient, a physiological characteristic of such a patient indicative of a respiratory cycle, and
  (c) changing said treatment level includes causing said dosage rate of medication to transition from a first predetermined dosage rate to a second predetermined dosage rate over said first predetermined number of respiratory cycles of such a patient by adjusting an output of said system for providing medication by said first predetermined amount over said second predetermined number of respiratory cycles of such a patient.

28. A method of treating a patient according to claim 21, wherein
(a) providing a therapeutic treatment includes:
generating a flow of breathing gas,
communicating said flow of breathing gas to an airway of a patient,
establishing a first gain, and
controlling one of a pressure and a flow of breathing gas provided to a patient based on a fluid characteristic signal and said first gain;
(b) detecting a respiratory cycle includes detecting, via a sensor, at least one fluid characteristic associated with a flow of breathing gas to a patient and providing said fluid characteristic signal corresponding to said detected characteristic; and
(c) changing said treatment level includes adjusting said first gain from a first predetermined level to a second predetermined level over said first predetermined number of respiratory cycles of such a patient by said first predetermined amount over said second predetermined number of respiratory cycles of such a patient.

29. A method of treating a patient according to claim 28, wherein detecting at least one fluid characteristic includes detecting a rate of said flow of breathing gas.

30. A method of treating a patient according to claim 28, wherein
(a) controlling one of a pressure and a flow of breathing gas provided to a patient includes controlling one of said pressure and said flow of breathing gas based on one of a base pressure and a base flow rate in addition to controlling said flow of breathing gas based on said first gain and said fluid characteristic signal, and
(b) changing said treatment level includes adjusting one of said base pressure and said base flow rate from a first predetermined level to a second predetermined level over a third predetermined number of respiratory cycles of such a patient by said predetermined amount over a fourth predetermined number of respiratory cycles of such a patient.

31. A method of treating a patient according to claim 21, wherein
(a) providing a therapeutic treatment includes:
generating a flow of breathing gas,
communicating said flow of breathing gas to an airway of a patient,
establishing a first gain and a second gain, and
controlling one of a pressure and a flow of breathing gas provided to a patient;
(b) detecting a respiratory cycle includes:
determining a rate of said flow of breathing gas provided to such a patient and providing a first signal corresponding to said rate of said flow of breathing gas, and
determining a volume of breathing gas provided to such a patient and providing a second signal corresponding to said volume,
wherein controlling one of a pressure and a flow of breathing gas provided to a patient includes controlling one of said pressure and said flow of breathing gas based on a first product of said first gain and said first signal in combination with a second product of said second gain and said second signal; and
(c) changing said treatment level includes adjusting at least one of said first gain and said second gain from a first predetermined level to a second predetermined level over said first predetermined number of respiratory cycles of such a patient by said first predetermined amount over said second predetermined number of respiratory cycles of such a patient.

32. A method of treating a patient according to claim 21, wherein
(a) providing a therapeutic treatment includes:
generating a flow of breathing gas,
communicating said flow of breathing gas to an airway of a patient,
controlling one of a pressure and a flow of breathing gas provided to a patient based on a product of a fluid characteristic signal and a gain in combination with one of a base pressure and a base flow rate;
(b) detecting a respiratory cycle includes detecting, via a sensor, at least one fluid characteristic associated with a flow of breathing gas to a patient and providing said fluid characteristic signal corresponding to said detected characteristic; and
(c) changing said treatment level includes adjusting one of said base pressure and said base flow rate from one of a first predetermined pressure level and a first predetermined flow rate to one of a second predetermined pressure level said a second predetermined flow rate over said first predetermined number of respiratory cycles of such a patient by said predetermined amount over said second predetermined number of respiratory cycles of such a patient.

33. A method of treating a patient according to claim 21, further comprising adjusting at least one of said first predetermined level, said second predetermined level, said first predetermined number of respiratory cycles, said second predetermined number of respiratory cycles, and said predetermined amount to control how said treatment changes over a plurality of respiratory cycles of such a patient.

* * * * *